(12) United States Patent
Yamazoe et al.

(10) Patent No.: US 9,791,375 B2
(45) Date of Patent: Oct. 17, 2017

(54) LIGHT MEASURING APPARATUS EMPLOYING OPTICAL ELECTRIC FIELD ENHANCING DEVICE

(71) Applicant: FUJIFILM Corporation, Tokyo (JP)

(72) Inventors: Shogo Yamazoe, Ashigarakami-gun (JP); Masayuki Naya, Ashigarakami-gun (JP); Megumi Shiota, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 149 days.

(21) Appl. No.: 14/668,500

(22) Filed: Mar. 25, 2015

(65) Prior Publication Data

US 2015/0198535 A1   Jul. 16, 2015

Related U.S. Application Data

(63) Continuation of application No. PCT/JP2013/005754, filed on Sep. 27, 2013.

(30) Foreign Application Priority Data

Sep. 28, 2012  (JP) ................. 2012-215406

(51) Int. Cl.
*G01J 3/44* (2006.01)
*G01N 21/00* (2006.01)
(Continued)

(52) U.S. Cl.
CPC .......... *G01N 21/658* (2013.01); *G01B 11/14* (2013.01); *G01J 3/0227* (2013.01); *G01J 3/4412* (2013.01); *G01N 2201/0612* (2013.01)

(58) Field of Classification Search
CPC ...... G01B 11/14; G01J 3/4412; G01N 21/658
(Continued)

(56) References Cited

U.S. PATENT DOCUMENTS

2003/0231304 A1   12/2003   Chan et al.
2004/0161369 A1    8/2004   Chan et al.
(Continued)

FOREIGN PATENT DOCUMENTS

JP         9-72848 A     3/1997
JP     2005-172569 A    6/2005
(Continued)

OTHER PUBLICATIONS

Japanese Office Action dated Oct. 27, 2015, for Japanese Application No. 2012-215406 with the English translation.
(Continued)

*Primary Examiner* — Sunghee Y Gray
(74) *Attorney, Agent, or Firm* — Birch, Stewart, Kolasch & Birch, LLP

(57) ABSTRACT

Using an optical electric field enhancing device including a fine uneven structure made of gold formed on the front surface of a transparent substrate, illumination light of a wavelength in the range from 400 to 530 nm is applied at least to an analyte, positional information of the analyte is detected by a position detection unit disposed on the rear surface side of the optical electric field enhancing device, and excitation light is applied to the detected position by an excitation light application unit. Signal light emitted from the analyte when the excitation light is applied is detected from the rear surface side of the transparent substrate.

11 Claims, 4 Drawing Sheets

(51) Int. Cl.
*G01N 21/65* (2006.01)
*G01B 11/14* (2006.01)
*G01J 3/02* (2006.01)

(58) Field of Classification Search
USPC .................. 356/301; 435/288.7; 422/82.05
See application file for complete search history.

(56) References Cited

U.S. PATENT DOCUMENTS

| | | | |
|---|---|---|---|
| 2005/0105085 | A1 | 5/2005 | Naya |
| 2008/0273199 | A1* | 11/2008 | Maier ...................... G01J 3/02 356/301 |
| 2011/0194106 | A1* | 8/2011 | Murakami ............. B82Y 30/00 356/301 |
| 2012/0019818 | A1* | 1/2012 | Wang ...................... G01J 3/10 356/301 |
| 2012/0212733 | A1* | 8/2012 | Kodali .................. B82Y 15/00 356/301 |
| 2013/0182248 | A1 | 7/2013 | Naya et al. |
| 2013/0182343 | A1 | 7/2013 | Naya et al. |

FOREIGN PATENT DOCUMENTS

| | | |
|---|---|---|
| JP | 2006-514286 A | 4/2006 |
| JP | 2006-145230 A | 6/2006 |
| JP | 4347801 B2 | 10/2009 |
| JP | 2012-63293 A | 3/2012 |
| JP | 2012-63294 A | 3/2012 |
| WO | WO 2010/016267 A1 | 2/2010 |

OTHER PUBLICATIONS

Ghadarghadr et al., "Plasmonic array nanoantennas on layered substrates: modeling and radiation characteristics", Optics Express, 2009, vol. 17, No. 21, pp. 18556-18570.
International Search Report, issued in PCT/JP2013/005754, dated Jan. 28, 2014.
Written Opinion of the International Searching Authority, issued in PCT/JP2013/005754, dated Jan. 28, 2014.

* cited by examiner

FIG.3
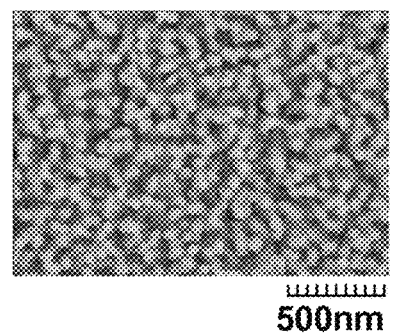
500nm
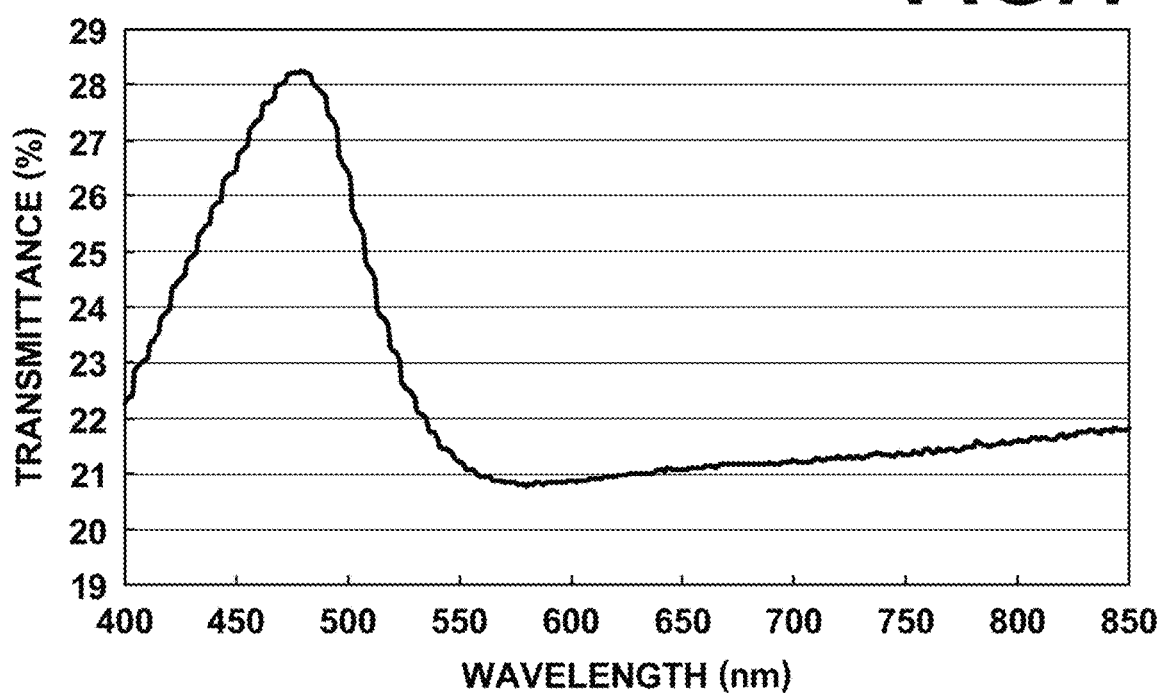
FIG.4

LIGHT MEASURING APPARATUS EMPLOYING OPTICAL ELECTRIC FIELD ENHANCING DEVICE

CROSS-REFERENCE TO RELATED APPLICATIONS

This application is a Continuation of PCT International Application No. PCT/JP2013/005754 filed on Sep. 27, 2013, which claims priority under 35 U.S.C. §119(a) to Japanese Patent Application No. 2012-215406 filed on Sep. 28, 2012. Each of the above applications is hereby expressly incorporated by reference, in its entirety, into the present application.

TECHNICAL FIELD

The present invention relates to a measuring apparatus for detecting signal light enhanced with an optical electric field enhancing device, which includes a fine uneven structure made of a metal capable of inducing localized plasmons, and measuring physical properties of the signal light.

BACKGROUND ART

Sensor devices and electric field enhancing devices, such as Raman spectroscopic apparatuses, using the electric field enhancing effect of the localized plasmon resonance phenomenon on the surface of a metal have been known. The Raman spectroscopy is a method to obtain a spectrum (Raman spectrum) of Raman-scattered light by separating scattered light which is obtained by applying single wavelength light to a material, and is used to identify materials, etc.

The Raman spectroscopy includes a Raman spectroscopy method called surface enhanced Raman (SERS), which uses optical electric fields enhanced by localized plasmon resonance in order to enhance weak Raman-scattered light (see S. Ghadarghadr et al., "Plasmonic array nanoantennas on layered substrates: modeling and radiation characteristics", Optics Express, Vol. 17, No. 21, pp. 18556-18570, 2009, hereinafter Non-Patent Literature 1). This uses a principle where, when light is applied to a metal body, in particular, a metal body having nano-order protrusions and recesses on the surface, which is in contact with a material, the optical electric fields are enhanced due to the localized plasmon resonance, and the intensity of Raman-scattered light from a sample in contact with the surface of the metal body is enhanced. The surface enhanced Raman spectroscopy can be performed by using a substrate having an uneven structure of a metal on the surface as a carrier (substrate) for carrying the analyte.

As the substrate having a fine uneven structure of a metal on the surface, a substrate which is formed by forming protrusions and recesses on the surface of a Si substrate and forming a metal film on the surface of the protrusions and recesses is mainly used (see PCT Japanese Publication No. 2006-514286, Japanese Patent No. 4347801, and Japanese Unexamined Patent Publication No. 2006-145230, hereinafter Patent Literature 1, 2, and 3, respectively).

Also, a substrate which is formed by anodizing a surface of an Al substrate to partially form a metal oxide layer ($Al_2O_3$), and filling a plurality of fine holes which are naturally formed in the surface of the metal oxide layer during the anodization with a metal has been proposed (see Japanese Unexamined Patent Publication No. 2005-172569, hereinafter Patent Literature 4).

The conventional optical electric field enhancing devices disclosed in Patent Literature 1 to 4 are formed by forming a fine uneven structure on the surface of an opaque substrate, such as Si or Al, and forming a metal film on the surface having the fine uneven structure or filling the recesses with the metal. Patent Literature 4 teaches an example where a transparent substrate, such as a glass substrate, is used; however, the fine uneven structure is made of an opaque material, such as silicon or germanium.

The conventional Raman spectroscopic apparatuses are configured to detect the Raman-scattered light from the sample-surface side. However, in a case where the analyte is a μm-order or larger sample, such as cells, the sample blocks the Raman-scattered light and it is difficult to receive the weak Raman-scattered light at high S/N.

The present inventors have developed, as an optical electric field enhancing device which allows the SERS measurement at good S/N, an optical electric field enhancing device formed by covering the surface of protrusions and recesses of a transparent fine uneven structure called boehmite with a metal film, such as gold. This device allows detecting the Raman-scattered light from the rear surface side of the sample, thereby allowing detecting signal light enhanced by the plasmon-enhanced optical electric fields without being blocked by the analyte (see Japanese Unexamined Patent Publication Nos. 2012-063293 and 2012-063294, hereinafter Patent Literature 5 and 6, respectively).

SUMMARY OF INVENTION

Technical Problem

When the SERS detection is performed, it is necessary to focus excitation light on the analyte, and, in order to detect the position of the analyte, it is necessary to illuminate the optical electric field enhancing device on which the analyte is placed.

In the case where the analyte has a large thickness or the analyte is in a liquid sample, it is difficult to accurately detect the position of the analyte. It is therefore believed to be preferred that the position detection be performed from the rear surface side, similarly to the detection of the signal light.

However, the optical electric field enhancing devices disclosed in Patent Literature 5 and 6 include the metal film on the surface, and have a problem that the amount of light detected by a position detector is decreased due to a loss caused by reflection, absorption, etc., of the illumination light. Further, if the intensity of illumination is increased to increase the detected amount of light, the temperature of the metal film absorbing the illumination light may rise and the analyte may be thermally damaged. In particular, if the analyte is a biological analyte, such as a cell or a metabolite thereof, degeneration or apoptosis may be caused by thermal stimulation and the analyte may die. It is therefore desirable that the temperature rising of the metal film be as small as possible.

In view of the above-described circumstances, the present invention is directed to providing a light measuring apparatus where weak light is enhanced using the light enhancing effect of localized plasmons and detected, the light measuring apparatus allowing highly accurate position detection of an analyte without thermally damaging S/N.

Solution to Problem

An measuring apparatus of the invention includes:

an optical electric field enhancing device including a transparent substrate, and a fine uneven structure made of gold formed on the front surface of the transparent substrate, wherein the fine uneven structure made of gold is capable of inducing localized plasmons when excitation light is applied, and an analyte is placed on the surface of the fine uneven structure;

an illumination optical system for applying illumination light of a wavelength in the range from 400 to 530 nm at least to the analyte;

a position detection unit disposed on the rear surface side of the optical electric field enhancing device, the position detection unit detecting a position of the analyte by detecting, from the rear surface side of the transparent substrate, light emitted from the analyte when the illumination light is applied to the analyte;

an excitation light application unit for applying excitation light to the position detected by the position detection unit; and a light detection unit disposed on the rear surface side of the optical electric field enhancing device, the light detection unit detecting, from the rear surface side of the transparent substrate, signal light emitted from the analyte when the excitation light is applied.

The term "transparent" as used herein refers to that the transmittance is 50% or more for the light applied to the fine uneven structure, the light emitted from the analyte due to said light, and the illumination light. The transmittance for these light is preferably 75% or more, and more preferably 90% or more.

The "illumination light of a wavelength in the range from 400 to 530 nm" as used herein refers to that, when the illumination light is applied from one side of the optical electric field enhancing device 10, 40% or more of the total amount of light (in the visible range from 400 to 750 nm) that is transmitted through to the other side is within this wavelength range.

It is preferred that the fine uneven structure made of gold has an average film thickness in the range from 10 to 150 nm.

The fine uneven structure made of gold may have a fine uneven structure depending on an uneven structure formed on a base substrate, or may have a fine uneven structure that does not depend on the surface shape of the base substrate. The fine uneven structure that is capable of inducing localized plasmons is typically an uneven structure where the average size and the average pitch of protrusions and recesses forming the uneven structure are smaller than the wavelength of the light.

Specifically, it is preferred that the average pitch of the protrusions and recesses and the distance (depth) between the apexes of the protrusions and the bottoms of the recesses are 200 nm or less.

The average pitch of the protrusions and recesses is found by taking an image of the surface of the fine uneven structure with a SEM (scanning electron microscope), performing image processing to binarize the image, and performing statistical processing.

The average depth of the protrusions and recesses is found by measuring the surface shape with an AFM (atomic force microscope), and performing statistical processing.

A preferred aspect of the optical electric field enhancing device includes a transparent substrate having a fine uneven structure on the front surface thereof, and a gold film formed on the surface of the transparent substrate. In this aspect, it is preferred that at least the fine uneven structure of the transparent substrate be made of bayerite or boehmite.

It is preferred that the illumination optical system be disposed on the rear surface side of the optical electric field enhancing device.

It is preferred that the excitation light application unit be disposed on the rear surface side of the optical electric field enhancing device, and apply the excitation light from the rear surface side of the transparent substrate.

It is preferred that the main component of the transparent substrate be a metal hydroxide, or a hydroxide of a metal oxide. The "main component" as used herein refers to a component contained in an amount of 90 mass % or more.

The measuring apparatus of the invention is also preferably used in an aspect where the optical electric field enhancing device includes a liquid sample holding member for holding a liquid sample on the fine uneven structure made of gold. In this aspect, the liquid sample holding member may include a liquid inlet port and a liquid outlet port.

It is preferred that a position adjusting means be provided, on which the optical electric field enhancing device is secured, and which is capable of moving the optical electric field enhancing device in the in-plane direction thereof such that the excitation light is applied to the position detected by the position detection unit.

The light detected by the light detection unit may be Raman-scattered light, surface enhanced Raman-scattered light, fluorescence, higher harmonic, Rayleigh scattered light, Mie scattered light, etc., and is preferably Raman-scattered light or surface enhanced Raman-scattered light.

The measuring apparatus of the invention is preferably usable with a biological analyte, such as a living tissue, a cell, a microorganism, a mycoplasma, a protein, etc.

Advantageous Effects of Invention

In the measuring apparatus of the invention, an analyte is placed on the optical electric field enhancing device which includes on the front surface the fine uneven structure made of gold capable of inducing localized plasmons, and at least the analyte is illuminated with light of a wavelength in the range from 400 to 530 nm to detect the position of the analyte with the position detection unit, which is disposed on the rear surface side of the optical electric field enhancing device. Then, excitation light is applied to the position, and signal light emitted from the analyte when the excitation light is applied is detected from the rear surface side of the transparent substrate. The optical electric field enhancing device can effectively induce localized plasmons on the surface of the fine uneven structure made of gold when the excitation light is applied, and can provide an optical electric field enhancing effect due to the localized plasmons. The signal light emitted from the analyte when light is applied to the analyte is enhanced by the optical electric field enhancing effect, and this allows highly sensitive detection of the signal light.

In the invention, signal light that is enhanced by the effect of the optical electric field enhancing device can be detected by performing the position detection using illumination light which contains a high ratio of light components within a specific wavelength range which can well transmit the gold film and are less likely to interfere with the main wavelength range of the excitation light and the signal light. Further, since the light (detection light) emitted from the analyte is detected from the rear surface side of the transparent substrate, light enhanced by the enhanced optical electric fields having the maximum intensity on the surface of the metal film can be detected without being blocked by the analyte. This allows highly accurate detection of the position of the analyte without thermally damaging the analyte, and measurement of physical properties of the signal light at good S/N.

BRIEF DESCRIPTION OF THE DRAWINGS

FIG. 3 shows a SEM picture of the top surface of a fine uneven structure made of gold, FIG. 4 shows a transmission spectrum of a gold film.

DESCRIPTION OF EMBODIMENTS

Figure 1:
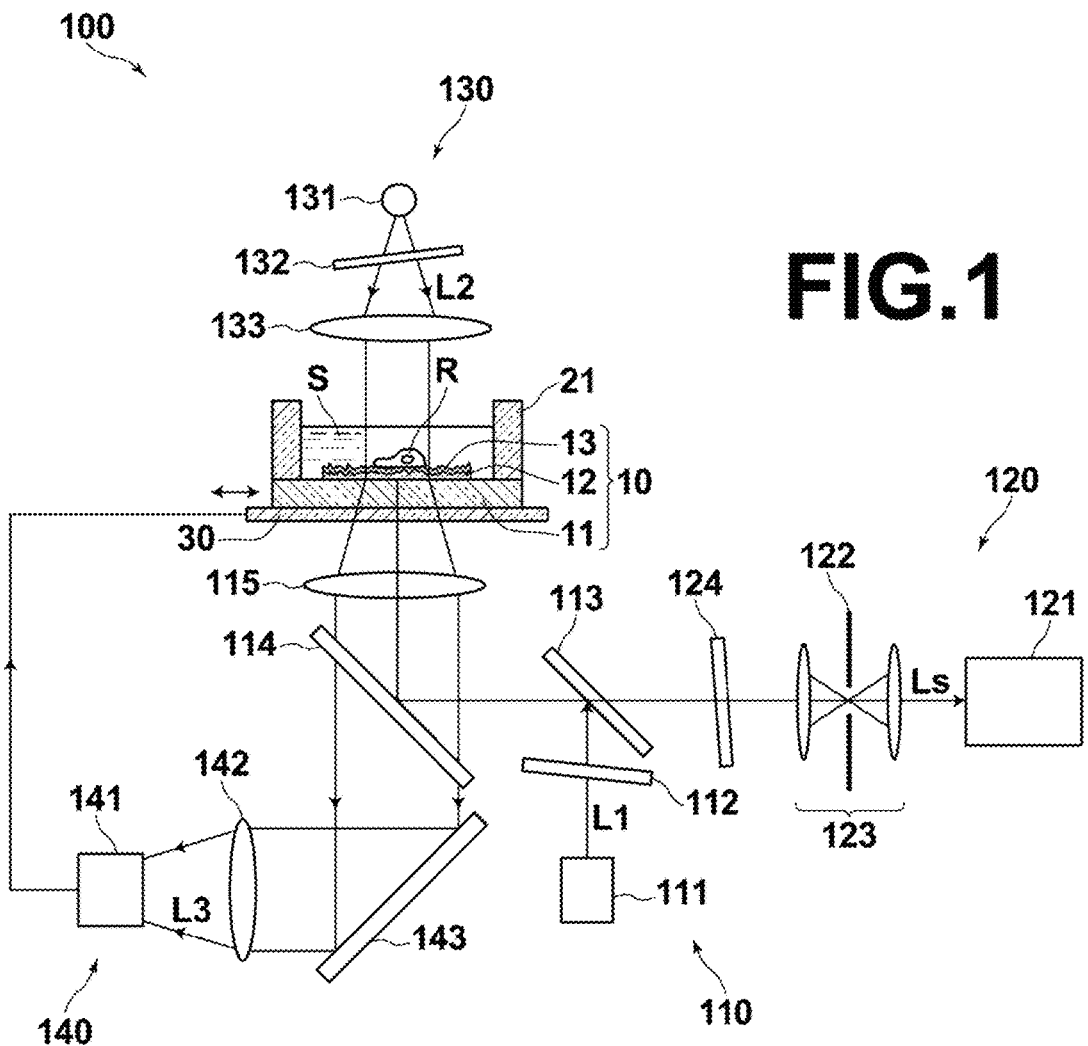
FIG. 1 is a schematic diagram illustrating the configuration of a Raman spectroscopic apparatus according to a first embodiment of a measuring apparatus of the present invention.

Hereinafter, embodiments of a measuring apparatus of the present invention are described with reference to the drawings. To facilitate visual recognition, the elements shown in the drawings are not to scale.

First Embodiment

As a first embodiment of the measuring apparatus of the invention, a Raman spectroscopic apparatus 100 is described. FIG. 1 is a schematic diagram illustrating the configuration of the Raman spectroscopic apparatus 100 according to the first embodiment.

As shown in FIG. 1, the Raman spectroscopic apparatus 100 includes: an optical electric field enhancing device 10 which supports an analyte R in a liquid sample S; an illumination optical system 130 which illuminates the analyte R on the optical electric field enhancing device 10 with illumination light L2; a position detection unit 140 which detects, from the rear surface side of a transparent substrate, light emitted from the analyte when it is illuminated with the illumination light L2 to detect the position of the analyte R; an excitation light application unit 110 which applies excitation light L1 to the position of the analyte from the rear surface side (transparent substrate side) of the optical electric field enhancing device 10; and a light detection unit 120 which detects, from the rear surface side of the optical electric field enhancing device 10, Raman-scattered light (signal light) Ls emitted from the analyte R and enhanced by operation of the optical electric field enhancing device 10.

In the Raman spectroscopic apparatus 100, the optical electric field enhancing device 10 is placed on a transparent stage (position adjusting means) 30 which is movable in the in-plane direction (the direction of the arrow in the drawing) of the substrate such that the excitation light L1 is applied to the analyte position detected by the position detection unit 140. Although the stage is provided as the position adjusting means in this embodiment, the aspect of the position adjusting means is not limited to a stage.

First, the optical electric field enhancing device 10 is described. FIG. 1 shows an aspect where a cell member 21 having a cylindrical side wall is provided on the transparent substrate 11 so that a liquid sample S can be held. However, this aspect is not intended to limit the invention.

Figure 2:
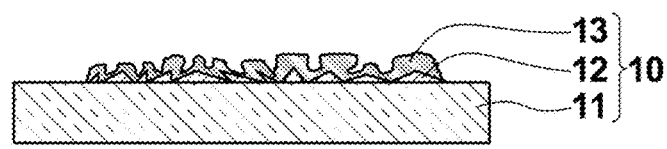
FIG. 2 is a sectional view illustrating an optical electric field enhancing device included in the Raman spectroscopic apparatus shown in FIG. 1.

FIG. 2 is a sectional view taken along the thickness direction of the optical electric field enhancing device 10 shown in FIG. 1. As shown in the drawing, the optical electric field enhancing device 10 includes, on a transparent substrate 11, a transparent fine uneven structure 12, and a fine uneven structure 13 made of gold which is formed on the transparent fine uneven structure 12. When the excitation light L1 is applied, localized plasmons are induced on the surface to form optical electric fields enhanced by localized plasmon resonance.

The average size and the average pitch of the protrusions of the protrusions and recesses of the fine uneven structure 13 made of gold are not particularly limited provided that the fine uneven structure 13 is capable of inducing localized plasmons on the surface when the excitation light L1 is applied. However, it is preferred that the average size and the average pitch be smaller than the wavelength of the excitation light L1. It is desirable that the fine uneven structure 13 made of a gold film has an average depth of 200 nm or less from the apexes of the protrusions to the bottoms of the recesses adjacent to the protrusions, and an average pitch of 200 nm or less between the apexes of the protrusions adjacent to each other with the recess therebetween.

The fine uneven structure 13 made of gold preferably has an average film thickness within the range from 10 to 150 nm, and more preferably from 30 to 100 nm. When the film thickness is within the above-described range, the signal light can well transmit the film, and a good electric field enhancing effect can be provided. It should be noted that, in the case where the fine uneven structure 13 is formed by forming the gold film on the transparent fine uneven structure, the average film thickness can be regarded as the film thickness of the formed gold film. For example, if the gold film is formed under the same conditions as those in a case where a gold film is formed on a flat glass substrate, one can estimate that the gold film having the same thickness as that of the gold film formed on the flat glass substrate is formed.

The fine uneven structure 13 made of gold may have a fine uneven structure depending on the uneven structure 12 formed on the base substrate, as in this embodiment, or may have a fine uneven structure that does not depend on the surface shape of the base substrate where the base substrate used has high surface smoothness.

The transparent substrate 11 is not particularly limited provided that it is transparent; however, the transparent substrate 11 with higher transparency is more preferred, and examples thereof include glass, acrylic resin, etc. The transparent substrate 11 may have a single layer structure or a multi-layer structure. The cell member (liquid holding means) 21 is not particularly limited, and may be made of the same material as the transparent substrate 11.

The transparent fine uneven structure 12 is not particularly limited provided that it has an average depth and an average pitch that allows inducing localized plasmons on the surface of the fine uneven structure 13 of the surface of the gold film formed on the transparent fine uneven structure 12. The transparent fine uneven structure 12 is preferably a bayerite layer or a boehmite layer, and is most preferably a boehmite layer in view of ease of film formation and high in-plane uniformity of the uneven structure. In the aspect where the optical electric field enhancing device 10 uses boehmite, the surface uneven structure has high in-plane uniformity, and this allows obtaining highly reproducible data when measurements are conducted on the same sample with applying the light to different positions on the sample. This allows improving the reliability of data by obtaining pieces of data of the same sample with applying the light to different positions on the sample.

As one example of the method for manufacturing the optical electric field enhancing device 10, an aspect where a boehmite layer is provided as the transparent fine uneven structure 12 is described.

First, the plate-like transparent substrate 11 is prepared, and the transparent substrate 11 is washed with pure water. Then, an aluminum layer having a thickness on the order of several tens nanometers is formed by sputtering on the surface of the transparent substrate 11.

Subsequently, the transparent substrate 11 provided with the aluminum layer is immersed in boiled pure water, and is removed from the boiled pure water after several minutes (around five minutes). This boiling treatment (boehmite treatment) makes the aluminum layer transparent to thereby form the transparent fine uneven structure (boehmite layer) 12.

On the thus obtained boehmite layer 12, a gold film is formed by vapor deposition, and thus the optical electric field enhancing device 10 is obtained. It should be noted that the method used to form the gold film is not limited to vapor deposition, and the gold film may be formed by immobilizing gold fine particles, for example. Further, the vapor deposition is not limited to a usual vapor deposition method, and an oblique vapor deposition method may be used. In the case where the gold film is formed on the boehmite layer 12, it is believed that the uneven shape of the fine uneven structure 13 made of gold usually conforms to the shape of the uneven structure 12 of the surface of the boehmite. However, since gold easily form aggregates, etc., the uneven shape of gold in this case has a different aspect from that of the uneven shape of the base.

Another example of the transparent fine uneven structure 12 is an anodized aluminum film which is obtained by anodizing aluminum and then removing unanodized portions of the aluminum. Although the transparent substrate 11 and the transparent fine uneven structure 12 are made of different materials in the aspect shown in this embodiment, the transparent fine uneven structure 12 may be formed by processing the surface of the transparent substrate 11. In this case, the transparent fine uneven structure 12 is integrated with the transparent substrate 11. This arrangement can be achieved by conducting lithography and dry etching on the surface of a glass substrate, for example.

The excitation light application unit 110 includes: an excitation light source 111 which emits the excitation light L1; a laser line filter 112 which makes the light L1 emitted from the excitation light source 111 into excitation light of a specific wavelength; a dichroic mirror 113 which reflects the excitation light L1 passed through the filter 112 toward the substrate 10; and a lens 115 which collects the excitation light L1 reflected by the dichroic mirror 113 and reflected by a hot mirror 114 onto an area of the optical electric field enhancing device 10 on which the analyte R is placed and collimates light from the analyte R. The hot mirror 114 is capable of reflecting light from the substrate 10, which contains the Raman-scattered light Ls emitted from the analyte R upon application of the excitation light L1 and enhanced, toward a light detection unit 120, and transmitting position detection light L3, which will be described later.

The light detection unit 120 includes: a notch filter 124 which is disposed on the rear surface side of the transparent substrate 11, absorbs the excitation light L1 contained in the light, which contains the Raman-scattered light Ls, reflected by the hot mirror 114 and transmitted through the dichroic mirror 113, and transmits the remaining light; and a slit 122 and a pair of lenses 123 which remove noise light and collimate and direct the Raman-scattered light Ls to a spectroscope 121. The spectroscope 121 separates the incoming Raman-scattered light Ls to obtain a Raman spectrum.

The optical electric field enhancing device 10 can effectively induce localized plasmons on the surface of the gold film when the excitation light L1 is applied, and can provide an optical electric field enhancing effect due to the localized plasmons. In the Raman spectroscopic apparatus 100, the Raman-scattered light (signal light) Ls emitted from the analyte R when the excitation light L1 is applied to the analyte R is enhanced by the optical electric fields enhancing effect, thereby allowing highly sensitive detection of the Raman-scattered light Ls.

Since the Raman-scattered light Ls emitted from the analyte R is detected from the rear surface side of the transparent substrate 11, the surface enhanced Raman-scattered light (SERS light), which is enhanced by the enhanced optical electric fields having the maximum intensity on the surface of the gold film, can be detected without being blocked by the analyte R.

The Raman spectroscopic apparatus 100 further includes an illumination optical system 130 and a position detection unit 140 for allowing accurately applying the excitation light L1 to the analyte R.

The illumination optical system 130 applies illumination light L2 of a wavelength in the range from 400 to 530 nm to at least the analyte R, and includes an illumination light source 131, such as a xenon lamp, a band pass filter 132 which transmits the light of a wavelength in the range from 400 nm to 530 nm, and a lens 133 which collimates the illumination light L2.

When the analyte R on the optical electric field enhancing device 10 is illuminated with the illumination light L2 passed through the lens 133, part of light emitted from the analyte R upon application of the illumination light L2 is transmitted as light L3 through to the transparent substrate 11.

The position detection unit 140 includes a mirror 143 and a condensing lens 142 which reflect and guide the position detection light (scattered light) L3 transmitted through the transparent substrate 11, collimated by the lens 115, and then transmitted through the hot mirror 114 to a position detecting means (image sensor) 141. The position detection unit 140 can obtain positional information of the analyte R by detecting, from the rear surface side of the transparent substrate 11 (from the rear surface side of the optical electric field enhancing device 10), the position detection light L3 emitted from the analyte R when the illumination light is applied. As described previously, the stage 30 is moved in the in-plane direction based on the positional information detected by the position detection unit 140 to allow accurately applying the excitation light L1 to the analyte R.

With the Raman spectroscopic apparatus 100, the position to which the excitation light L1 is applied is controlled based on the obtained position detection information. This allows highly accurate application of the excitation light to the analyte R, thereby improving accuracy of the measurement. In an aspect of this embodiment, the position adjusting means may be one on which the optical electric field enhancing device 10 is secured and which is capable of moving the optical electric field enhancing device 10 in the in-plane direction such that the excitation light L1 is applied to the position detected by the position detection unit 140.

As stated in the "Technical Problem" section, it is necessary to focus the excitation light on the analyte when the SERS light detection is preformed. In the case where a device including a metal film on the surface, as with the optical electric field enhancing device 10, is used to hold the analyte, the amount of light detected by the position detector is decreased due to a loss caused by reflection, absorption, etc., of the illumination light used to detect the position of the analyte. If the intensity of the illumination is increased to increase the detected amount of light, the temperature of the metal film absorbing the illumination light may rise and the analyte may be thermally damaged.

The present inventors have studied arrangements that can reduce the temperature rising of the metal film as small as possible and can achieve highly accurate detection of the signal light (Raman-scattered light). Then, the present inventors have found that such detection can be achieved by performing the position detection using the illumination light L2 which contains a high ratio of light components within a specific wavelength range which can well transmit the gold film and are less likely to interfere with the main wavelength range of the excitation light.

First, the present inventors measured a transmission spectrum of a gold film and examined the peak transmittance wavelength range. An evaluation device for evaluating the transmission spectrum of a gold film was prepared by forming an aluminum film having a film thickness of 20 nm on a square glass substrate having a thickness of 0.5 mm and sides of 20 mm, immersing the glass substrate with the aluminum film in boiling pure water and removing the glass substrate with the aluminum film from the boiling pure water after five minutes to form boehmite, and forming a gold film having a film thickness of 30 nm on the boehmite by vapor deposition. Then, transmittance of the thus prepared evaluation device was measured using a spectroscope, U-4000 available from Hitachi, Ltd., where the measurement range was from 400 nm to 850 nm and the resolution was 1 nm. The results are shown in FIG. 4. The peak transmittance wavelength range was determined to be the range in which the transmittance was not less than 22%, which is the bottom value around a wavelength of 850 nm shown in FIG. 4.

Next, the present inventors studied influence on the accuracy of the signal light detection. It is believed that the illumination light L2 which contains less light of the wavelength range that is likely to interfere with the excitation light L1 has less influence on the accuracy of the detection of the signal light Ls which is enhanced by the effect of the optical electric field enhancing device 10.

In the case where the analyte is, in particular, a biological analyte, such as a living tissue, a cell, a microorganism, a mycoplasma, a protein, etc., light of a wavelength longer than 600 nm, which induces relatively low fluorescence (noise) from the analyte, is often used as the excitation light L1. Using light of a wavelength in the range from 400 nm to 530 nm can also reduce the interference with the excitation light L1.

Using the light of a wavelength in the range from 400 nm to 530 nm as the illumination light L2 of the Raman spectroscopic apparatus 100 therefore allows highly accurate detection of the position of the analyte without thermally damaging the analyte and measurement of physical properties of the signal light at good S/N.

It should be noted that, if a light-emitting diode, a semiconductor laser, or the like, is used as the illumination light source 131 in the illumination optical system 130, the band pass filter 132 is not necessary, and this is preferred in view of space saving and cost reduction. In addition, such light sources have low power consumption.

Further, if the illumination light source 131 is a semiconductor laser, the illumination light has a narrow line width of 10 nm or less. This allows concentrating the illumination light on the transmittance peak of the optical electric field enhancing device 10, and a higher effect of reducing the temperature rising is expected. However, semiconductor lasers have a problem of speckle noise, and it is necessary to take a measure to remove the noise, such as making the illumination light pass through a diffuser, or the like, before the illumination light is applied to the analyte.

Second Embodiment

Figure 5:
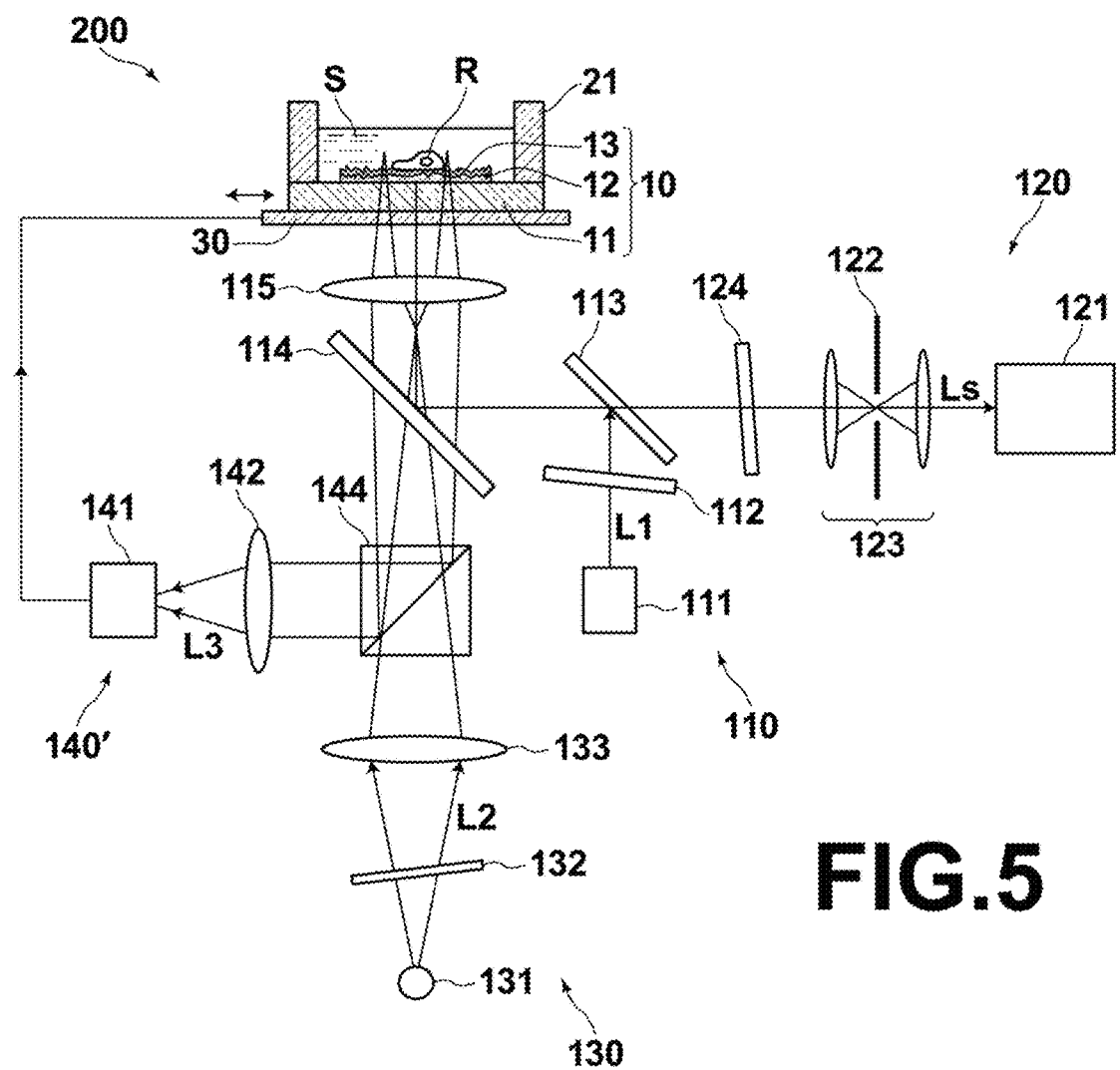
FIG. 5 is a schematic diagram illustrating the configuration of a Raman spectroscopic apparatus according to a second embodiment of the measuring apparatus of the invention.

As a second embodiment of the measuring apparatus of the invention, a Raman spectroscopic apparatus 200 is described. FIG. 5 is a schematic diagram illustrating the configuration of the Raman spectroscopic apparatus 200 according to the second embodiment. The elements that are the same as those of the Raman spectroscopic apparatus 100 are designated by the same symbols and a detailed explanation thereof is omitted.

In the Raman spectroscopic apparatus 200 shown in FIG. 5, the illumination optical system 130 is disposed on the rear surface side of the optical electric field enhancing device 10. In the first embodiment, where the illumination optical system 130 is disposed on the analyte R side, the position detection unit 140 includes the mirror 143 that reflects and guides the position detection light L3 transmitted through the hot mirror 114 to the position detecting means (image sensor) 141; whereas, in this embodiment, a position detection unit 140' includes a half beam splitter 144 in place of the mirror.

This arrangement allows reducing absorption of the illumination light L2 by the analyte R and the environment around the analyte R (such as the liquid sample) and reducing optical damage and thermal stimulation to the analyte R when compared with the first embodiment.

Further, the absence of the illumination optical system 130 on the analyte side facilitates disposing a terminal of a unit for monitoring the environment (such as temperature, humidity, oxygen concentration, pH, etc.) around the analyte on the analyte side, and also facilitates providing a circulation cell-type optical electric field enhancing device.

Figure 6:
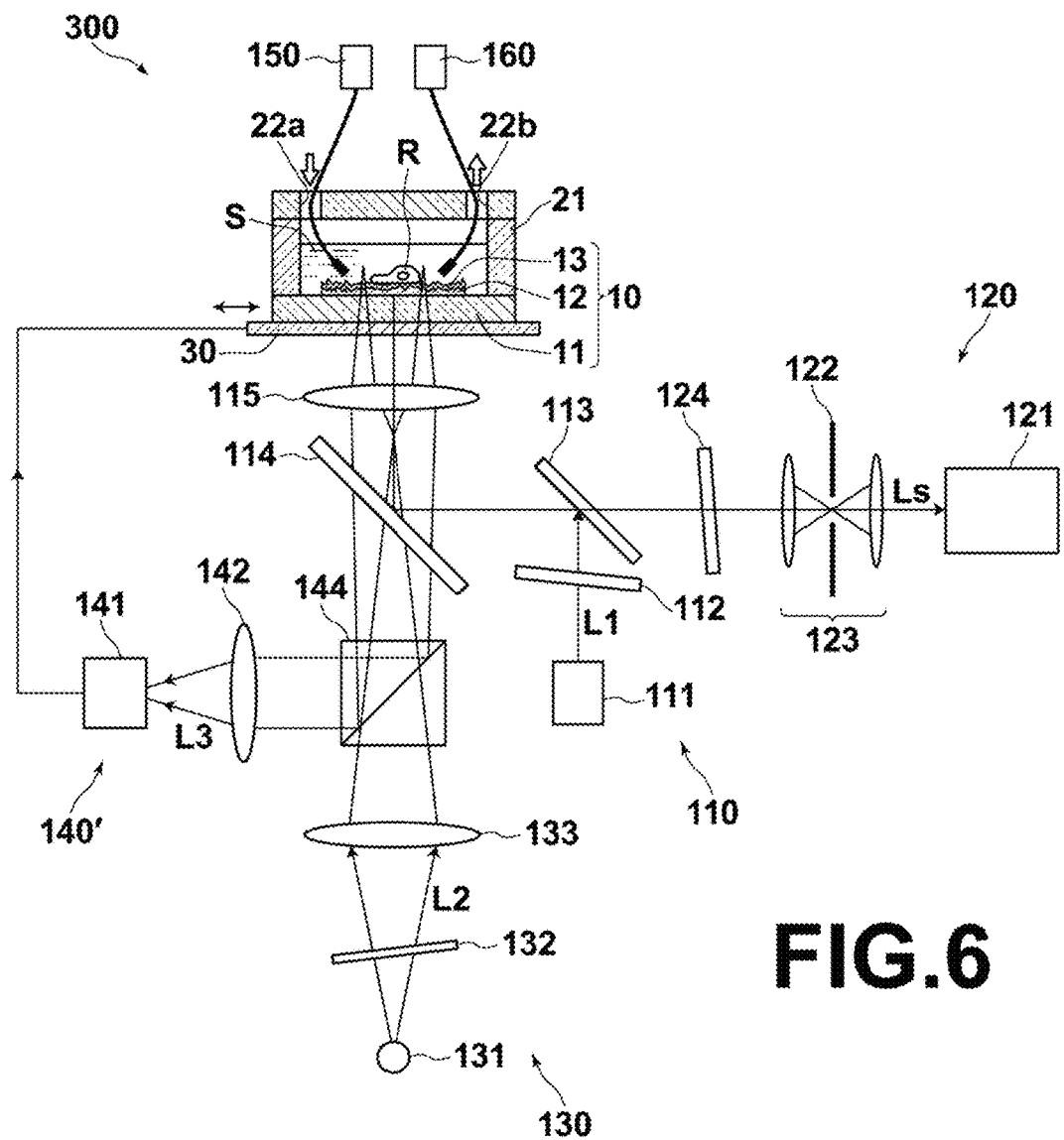
FIG. 6 shows a modification of the Raman spectroscopic apparatus shown in FIG. 5.

FIG. 6 illustrates the configuration of a Raman spectroscopic apparatus 300, which is a circulation cell-type optical electric field enhancing device including a liquid inlet port 22a and a liquid outlet port 22b, and includes a temperature monitoring unit 150 and an oxygen concentration monitoring unit 160. The Raman spectroscopic apparatus 300 is the same as the Raman spectroscopic apparatus 200 except that the shape of the cell for holding the liquid sample S is of a circulation cell, and the monitoring units 150 and 160 are provided.

In the case where the optical electric field enhancing device is of circulation cell type, tube connectors (not shown) which are connected to a tubing pump (not shown) are secured to the liquid inlet port 22a and the liquid outlet port 22b. The circulation cell-type optical electric field enhancing device allows circulating the liquid around the analyte by pumping the liquid in and out.

The temperature and the oxygen concentration of the liquid can be controlled while the liquid is circulated, and this allows maintaining or changing the environment around the analyte at or to desired values. However, while the temperature around the analyte can be controlled by circulating the liquid, local heating at the contact surface between the analyte R and the fine uneven structure 13 made of gold cannot be controlled by circulating the liquid. By configuring the Raman spectroscopic apparatus 300 to reduce the temperature rising of the fine uneven structure 13 due to the illumination light L3, highly accurate position detection of the analyte can be performed without thermally damaging the analyte and physical properties the signal light can be measured at good S/N.

Further, in the Raman spectroscopic apparatus 300, the illumination optical system 130 is disposed on the rear surface side of the optical electric field enhancing device 10, and this allows disposing the terminals of the temperature monitoring unit 150 and the oxygen concentration monitoring unit 160 in the vicinity of the analyte R. In this case, detection of the Raman-scattered light while monitoring the measurement environment around the analyte R, thereby allowing maintaining good measurement environment to perform the measurement with even higher accuracy.

Modifications

In the above-described embodiments, the excitation light application unit 110 and the light detection unit 120 are disposed on the rear surface side of the optical electric field enhancing device 10, and the excitation light is applied from the rear surface side. However, the excitation light application unit 110 may be disposed on the front surface side (the surface on which the analyte is placed) of the optical electric field enhancing device 10, and the excitation light may be applied from the front surface side. The localized plasmon resonance can be similarly induced and the optical electric field enhancing effect can be similarly obtained when the excitation light is applied from either of the front surface side or the rear surface side of the fine uneven structure made of a metal of the optical electric field enhancing device.

The optical electric field enhancing device 10 may include, on the rear surface side thereof, a second transparent fine uneven structure layer. The second transparent fine uneven structure layer functions as an anti-reflection film when the light is applied. The second fine uneven structure layer may be similar to the transparent fine uneven structure layer 12 provided on the front surface of the transparent substrate 10, and is preferably a boehmite layer.

In the Raman spectroscopic apparatuses of the above-described embodiments, the light Ls detected by the light detection unit 120 is Raman-scattered light. However, the same advantageous effects can be obtained with a measuring apparatus where the detected light Ls is fluorescence, higher harmonic, Rayleigh scattered light, Mie scattered light, etc.

What is claimed is:

1. A measuring apparatus comprising:
an optical electric field enhancing device comprising a transparent substrate, and a fine uneven structure made of gold formed on a front surface of the transparent substrate, wherein the fine uneven structure made of gold is capable of inducing localized plasmons when excitation light is applied, and an analyte is placed on a surface of the fine uneven structure;
an illumination optical system for applying illumination light only of a wavelength in a range from 400 to 530 nm at least to the analyte;
a position detection unit disposed on a rear surface side of the optical electric field enhancing device, the position detection unit detecting a position of the analyte by detecting, from the rear surface side of the transparent substrate, light emitted from the analyte when the illumination light is applied to the analyte;
an excitation light application unit for applying excitation light to the position on the optical electric field enhancing device; and
a light detection unit disposed on the rear surface side of the optical electric field enhancing device, the light detection unit detecting, from the rear surface side of the transparent substrate, signal light emitted from the analyte when the excitation light is applied,
wherein the optical electric field enhancing device comprises a transparent substrate having a fine uneven structure on the front surface thereof, and a fine uneven structure made of gold formed on the front surface of the transparent substrate, and
wherein a main component of the fine uneven structure of the transparent substrate is a metal hydroxide, or a hydroxide of a metal oxide.

2. The measuring apparatus as claimed in claim 1, wherein the illumination optical system is disposed on the rear surface side of the optical electric field enhancing device.

3. The measuring apparatus as claimed in claim 1, wherein the excitation light application unit is disposed on the rear surface side of the optical electric field enhancing device, and applies the excitation light from the rear surface side of the transparent substrate.

4. The measuring apparatus as claimed in claim 1, wherein at least the fine uneven structure of the transparent substrate is made of bayerite or boehmite.

5. The measuring apparatus as claimed in claim 1, wherein the fine uneven structure made of gold has an average film thickness in the range from 10 to 150 nm.

6. The measuring apparatus as claimed in claim 1, wherein the optical electric field enhancing device comprises a liquid sample holding member for holding a liquid sample on the fine uneven structure made of gold on the transparent substrate.

7. The measuring apparatus as claimed in claim 6, wherein the liquid sample holding member of the optical electric field enhancing device comprises a liquid inlet port and a liquid outlet port.

8. The measuring apparatus as claimed in claim 1, further comprising a position adjusting means on which the optical electric field enhancing device is secured, the position adjusting means being capable of moving the optical electric field enhancing device in an in-plane direction thereof such that the excitation light is applied to the position detected by the position detection unit.

9. The measuring apparatus as claimed in claim 1, wherein the light detected by the light detection unit is Raman-scattered light or surface enhanced Raman-scattered light.

10. The measuring apparatus as claimed in claim 1, wherein the analyte is any of a living tissue, a cell, a microorganism, a mycoplasma, and a protein.

11. The measuring apparatus as claimed in claim 1, wherein the illumination optical system applies illumination light only of a wavelength in the range from 430 to 510 nm nm.

* * * * *